United States Patent
Brook et al.

(10) Patent No.: US 10,610,902 B1
(45) Date of Patent: Apr. 7, 2020

(54) SPRAY NOZZLE USING ADVANCED OXIDATION

(71) Applicants: Cherie L. Brook, Owens Crossroads, AL (US); Ronald L. Barnes, Owens Crossroads, AL (US)

(72) Inventors: Cherie L. Brook, Owens Crossroads, AL (US); Ronald L. Barnes, Owens Crossroads, AL (US)

( * ) Notice: Subject to any disclaimer, the term of this patent is extended or adjusted under 35 U.S.C. 154(b) by 36 days.

(21) Appl. No.: 15/585,137

(22) Filed: May 2, 2017

Related U.S. Application Data (60) Continuation-in-part of application No. 14/798,821, filed on Jul. 14, 2015, now Pat. No. 9,636,715, which is a division of application No. 14/248,292, filed on Apr. 8, 2014, now Pat. No. 9,079,227.

(60) Provisional application No. 61/809,776, filed on Apr. 8, 2013, provisional application No. 62/408,690, filed on Oct. 14, 2016.

(51) Int. Cl.
| | |
|---|---|
| *B08B 3/02* | (2006.01) |
| *B01F 3/04* | (2006.01) |
| *D06F 35/00* | (2006.01) |
| *B05B 7/24* | (2006.01) |
| *A61L 2/22* | (2006.01) |
| *B01F 5/04* | (2006.01) |
| *A47L 15/42* | (2006.01) |
| *B05B 7/04* | (2006.01) |
| *B05B 5/16* | (2006.01) |
| *B05B 5/03* | (2006.01) |
| *A61L 2/18* | (2006.01) |
| *B05B 7/00* | (2006.01) |
| *B05B 1/04* | (2006.01) |

(52) U.S. Cl.
CPC ............ *B08B 3/026* (2013.01); *A47L 15/424* (2013.01); *A61L 2/183* (2013.01); *A61L 2/22* (2013.01); *B01F 3/04099* (2013.01); *B01F 5/0413* (2013.01); *B05B 5/03* (2013.01); *B05B 5/1608* (2013.01); *B05B 7/0483* (2013.01); *B05B 7/2402* (2013.01); *D06F 35/001* (2013.01); *A47L 15/4278* (2013.01); *B01F 2003/04886* (2013.01); *B05B 1/04* (2013.01); *B05B 7/0012* (2013.01); *B05B 7/0425* (2013.01); *B05B 7/2464* (2013.01)

(58) Field of Classification Search
None
See application file for complete search history.

(56) References Cited

U.S. PATENT DOCUMENTS 5,536,400 A * 7/1996 Schultz ................ A61L 2/10
210/192

* cited by examiner

*Primary Examiner* — Eric W Golightly
(74) *Attorney, Agent, or Firm* — Patent Grove LLC; Tomas Friend (57) ABSTRACT

A method for dispensing a sanitizing composition comprising a carrier fluid involves passing a carrier fluid under pressure through a nozzle and a chamber mounted to the nozzle. The chamber receives the carrier fluid from the nozzle and has an opening on an opposite side from the nozzle through which the carrier fluid exits the chamber. Ozone is provided to an interior of the chamber in the presence of the carrier fluid, and is irradiated with ultraviolet radiation as the carrier fluid and the ozone pass through an interior of the chamber.

11 Claims, 5 Drawing Sheets

SPRAY NOZZLE USING ADVANCED OXIDATION

CROSS REFERENCE TO RELATED APPLICATIONS

This application claims priority to U.S. 62/408,690 filed Oct. 14, 2016 and is a continuation-in-part of Applicant's U.S. patent application Ser. No. 14/798,821, filed Jul. 14, 2015, which issued as U.S. Pat. No. 9,636,715 on May 2, 2017; which is a divisional of Applicant's patent application Ser. No. 14/248,292, filed Apr. 8, 2014, now U.S. Pat. No. 9,079,227, which in turn claims priority from Applicant's U.S. provisional application No. 61/809,776, filed Apr. 8, 2013. Applications 62/408,690, 14/798,821, 14/248,292 and 61/809,776 are all hereby incorporated herein in their entireties by reference.

FIELD OF THE INVENTION

This application relates to spray heads for dispensing a solution for cleaning, and particularly to a spray head for dispensing a solution containing ozone reaction products for facilitating advanced oxidation reactions used for cleaning and sanitizing.

BACKGROUND OF THE INVENTION

Spray systems for dispensing cleaning solutions are well-known, and range from small, handheld bottles having a trigger-operated pump and spray nozzle to pressure washers that can develop thousands of pounds of pressure, and which can dispense a cleaning solution along with pressurized water. For handheld spray bottles, a dilute cleaning solution containing soaps, surfactants, bleaches and the like is contained within the bottle, and a trigger connected to a pump is operated to dispense the solution as a spray or stream. Larger systems, such as a pressure washer, are connected to a separate source of water, and pressurize the water to, in most cases, over 1,000 PSI. A separate container of a concentrated cleaning solution is provided, and which is metered into the high-pressure stream of water. In other systems, steam cleaners and/or pressure washers are used in butcher shops in conjunction with steam, soap solutions, disinfectant solutions and rinses to clean and sanitize surfaces contacted by meat.

Cruise ships in particular have problems with spread of various diseases among passengers due to crowded conditions, and the preparation of 4-6 meals a day. In particular, Norovirus and *E. Coli* can infect hundreds of people even on a relatively short cruise. While passengers and crew are instructed in health and cleanliness matters and these ships are thoroughly cleaned after each cruise, problems still persist.

Ozone is one of the most effective sanitizers known, and is more effective than chlorine as a disinfectant. It is also one of the safest and most convenient to use, because ozone breaks down into oxygen and leaves no harmful residues. However, its lifespan as a sanitizer is short due to its high reactive potential. Further, the byproducts of ozone, such as peroxides, free radicals and others, collectively known as "ozonites", are also high in reactive potential and useful for cleaning and sterilizing. As such, ozonites must be used immediately after they are created.

In other applications. It is desirable to clean and sanitize surfaces without ozone due to outgassing of ozone from a cleaning solution, or due to undesirable properties of the ozone itself. Here, cleaning of, for instance a carpet using water and ozone, may cause bleaching and/or weakening of strands of the carpet fabric. In other applications such as a commercial dishwasher in a restaurant, undesirable outgassing of ozone may occur where ozone mixed with water is applied as a last sanitizing step in the dishwashing process. In other applications such as icemakers used to make ice for drinks or keeping food fresh, or for sterilizing water used to make ice, ozone is undesirable because of its potential for altering the taste of food and drinks exposed to the ozone. In applications such as butcher shops and meatpacking plants, which are enclosed areas that are required to be sterilized on a daily basis, outgassing of ozone may cause irritation to lungs and breathing passages of workers.

As noted above, ozone reaction products, or "ozonites", have been discovered to be potent sanitizers in themselves. As such, Applicant proposes to use ozonites to promote advanced oxidation in order to sterilize various articles and surfaces. However, at least some of the more powerful ozonites have short reaction times, and are most advantageously used as soon as possible after being created.

DETAILED DESCRIPTION OF THE DRAWINGS

A cleaning system including at least ozone and a cleaning solution or solvent is disclosed. A spray head is provided that can be configured or fabricated to fit many cleaning implements, such as pressure washers, hand held, manually operated pumps, or spray heads can be built into cleaning machines such as dishwashers. In some embodiments, the ozone generator that creates ozone for the spray head may be used in conjunction with a halogen salt generator that also mixes a halogen, such as chlorine, bromine or even iodine, to the solution from the spray head. In other embodiments, reaction products from the chlorine generation process, such as NaOH, hydroxyl radicals, peroxides, a halogen salt, oxygen, and others, may also be mixed into the cleaning solution by the spray head, or mixed into the cleaning solution prior to being sprayed by the spray head. In yet other embodiments, ozone, chlorine and reaction products may be combined with a conventional cleaning soap or other cleaning compounds. In some embodiments, a spray nozzle may be configured to dispense steam, as from a steam cleaner, with any or all of ozone, a halogen such as chlorine and reaction products from generating chlorine from a chlorine generator inserted into the steam from the spray nozzle.

Figure 1:
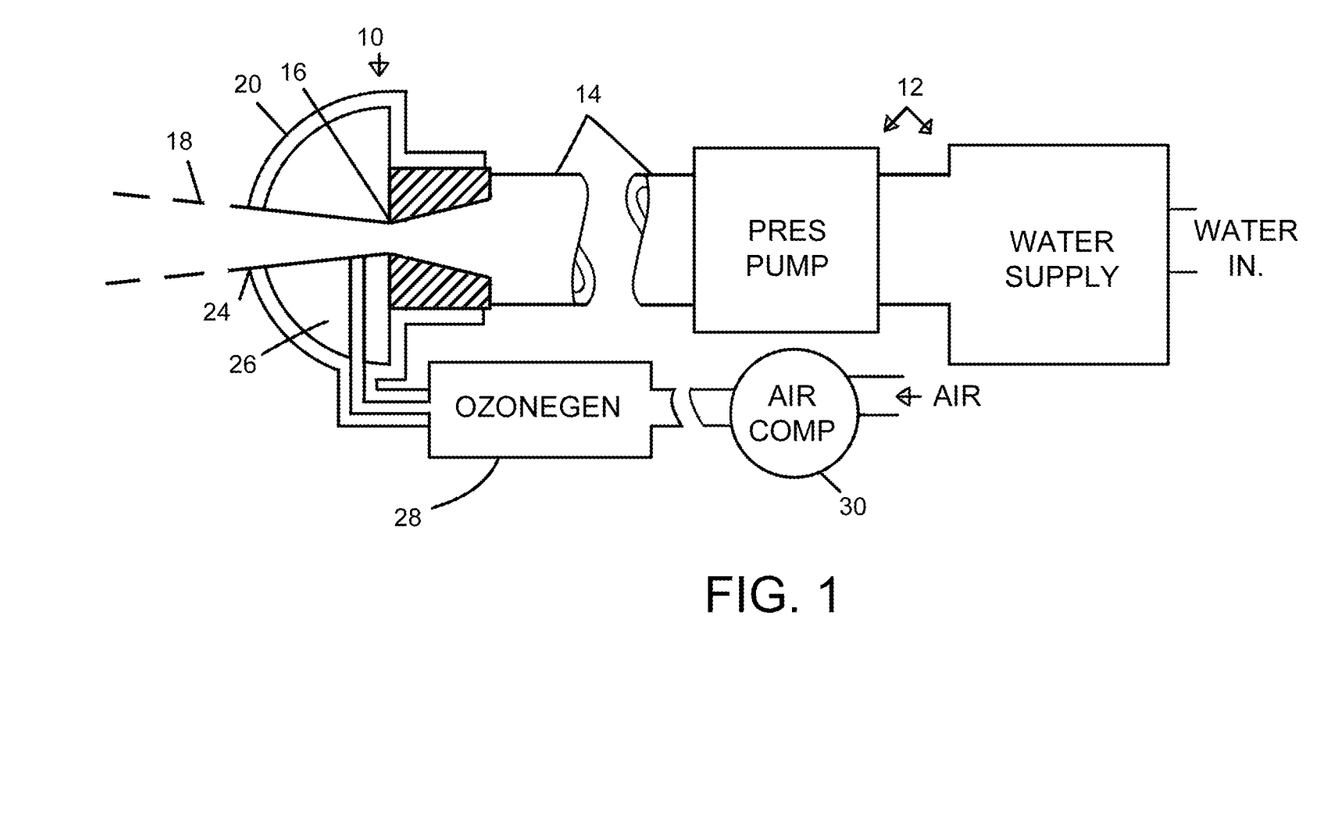
FIG. 1 is a diagrammatic view of a disinfection and cleaning system of the invention.

Referring to FIG. 1, a simplest embodiment is shown. Here, a spray nozzle 10 may be fitted to a pressure washer, a dishwasher or the like, or a hose similar to a garden hose and connected to a pressurized source of water, a steam cleaner or even a hand-held spray bottle manually operated by a trigger, all these devices illustrated graphically by water supply and pump 12, and which is configured so that a carrier fluid, such as pressurized water, steam or a cleaning solution, is passed through a tube 14 that leads to nozzle 10. Nozzle 10 is configured having an outlet or orifice 16 through which the water or cleaning solution 18 is forced in a stream or spray, which may be a high-pressure stream, or which may be a lower pressure stream, or a spray for wider area coverage and sanitization. A chamber or plenum 20 generally surrounds outlet or orifice 16, which is tapered as shown on its inner side in order to speed up the flow in a similar manner as a Venturi. This causes the stream to expand after it passes from orifice 16, and also develops a suction within chamber or plenum 20. The expanded stream passes from chamber or plenum 20 through an opening 24; which is typically larger than orifice 16, and may have different configurations. For instance, opening 24 may be configured as a slot in order to develop a fan-shaped spray, or may be round to develop a collimated stream or spray. The open end of tube or the like 26 is positioned near orifice 16 so that the suction developed by the stream issuing from internally tapered orifice 16 is felt at the open end of tube 26, and which draws at least ozone from ozone generator 28 into stream 18 just prior to the stream issuing from the spray nozzle. As such, the ozone is generated and mixed in stream 18 immediately as the stream is passed from nozzle 10. This appears to be one of the most effective ways to use ozone by itself as a sanitizer in the instant invention. A compressor 30 may be used to force air through ozone generator 30 into chamber 20 for positive control over the flow of air and ozone. In some embodiments, the compressor may be used as a regulator to limit airflow through the ozone generator in order to develop higher concentrations of ozone.

Ozone generator 28 may be an ultraviolet ozone producing lamp, a corona discharge device or any other ozone-producing device. For example, one ozone generator might be an ozone generator as described in Applicant's PCT application no. PCT/US2013/043485, filed 30 May 2013, which is incorporated in its entirety herein by reference, and which may also be configured to provide a flow of irradiated and sterilized water as water supply 12. In any case, ozone generator 28 provides ozone via tube 26 to a point within plenum 20 immediately adjacent stream 18 where Venturi suction is strongest. Typically, anti-backflow valves (not shown) are provided in tube 26 so that water cannot flow back into the ozone generator. As noted, in some embodiments, an air compressor 30 may be provided to actively pump oxygen or air through ozone generator 28, while in other embodiments oxygen or air may be drawn through ozone generator 28 by Venturi action developed by the end of tube 26 being in or closely proximate to stream 18. In yet other embodiments, air or oxygen may be provided to the ozone generator and subsequently to tube 26 from a pressurized container, a pressure swing oxygen concentrator or other similar device. As noted, spray head 20 may be any spray head, such as a pressure washer, spray heads in dishwashers, a manually operated spray bottle, or any other application where ozone is needed in a stream or spray of water 18. As such, a stream of water containing ozone may be used as an effective rinsing and sanitizing solution, such as on a cruse ship or in a rinse procedure during cleaning of a butcher shop or the like.

Figure 2:
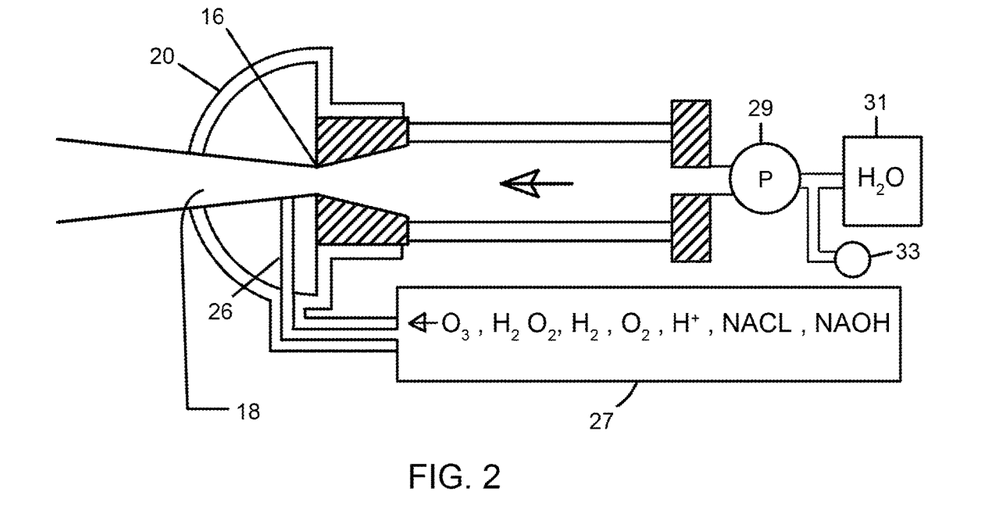
FIG. 2 is a partially cut-away, partially diagrammatic view of a cleaning and disinfection system of the invention.

In other embodiments, and referring to FIG. 2, a spray head 20 as described above including chamber 20 and tube 26 is connected to one or more of a source 27 of ozone, hydrogen peroxide, oxygen, hydroxyl radicals, a salt, sodium hydroxide, potassium hydroxide, silver, zinc, tin and copper compounds or any other beneficial compound or element, and which may be in addition to soap or another cleaning compound. In this embodiment, the compounds and elemental ions of source 27 would be dissolved in water, and drawn by Venturi action into stream 18. A pump 29 or source of pressurized water drives water through orifice 16 to develop spray 18. In some embodiments, source 31 may be independent of a residential supply, such as where the apparatus is portable, as by being configured as a cart, hand-carried or configured as a backpack-type device. In some embodiments, at least some of the substances may be provided prior to pump 29 in order to promote mixing of the substances by the pump.

Figure 3:
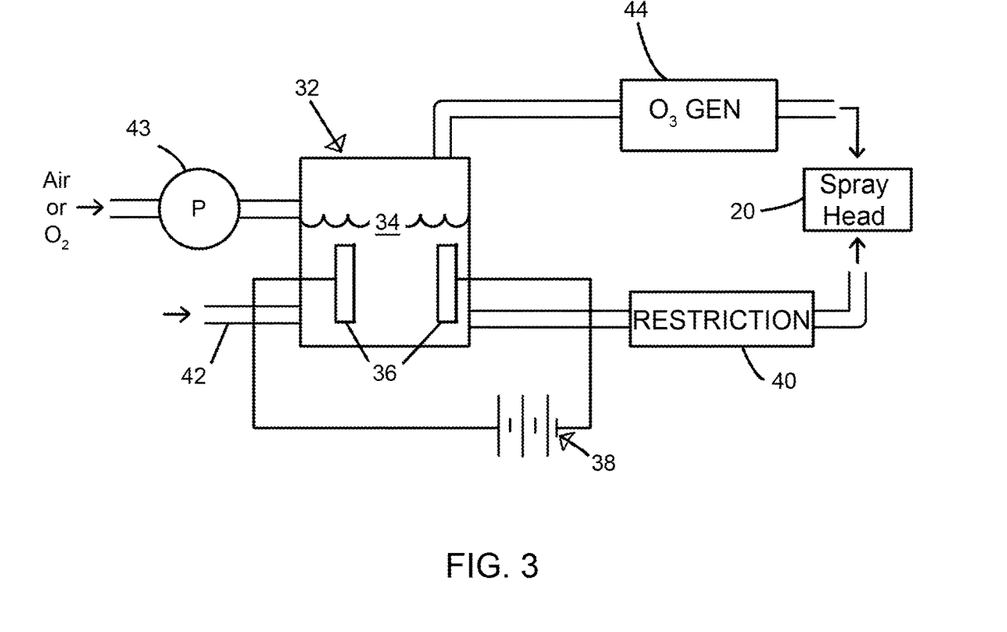
FIG. 3 is a block diagram of another embodiment of the invention.

As shown in FIG. 3, at least some of such substances may be provided by a halogen salt generator 32 containing a halogen salt solution 34. A pair of electrolysis plates 36 are provided, the plates having a sufficient voltage potential applied to them, as by a DC power source 38, so as to electrolyze the halogen salt and release a sanitizing halogen, such as chlorine, bromine or iodine. In some embodiments the halogen salt supply 34 remains relatively constant until depleted, whereupon the supply is changed, while in other embodiments a flow of the halogen salt solution and reaction products is applied to spray head 20 via a restriction 40. Restriction 40 limits the quantity of fluid from supply 34 that is allowed to flow to spray head 20. In some embodiments, the flow may be controlled at an inlet 42 at a predetermined rate, as by a manually set valve, or an automatically set valve responsive to a liquid level sensor, a flow rate sensor or other sensor for sensing quantity of fluid in ozone generator 32. In other embodiments, the fluid in halogen generator 32 may be drawn through the halogen generator by Venturi action developed by spray head 20. In addition, a residual of halogen that escapes from halogen supply 34 is applied along with air or oxygen through ozone generator 44, and subsequently to spray head 20. In some embodiments, an air pump 43 may be provided either to boost the supply of air or to regulate the air flow as noted above. In some embodiments, a flow of the halogen salt solution may be recirculated between a reservoir and the halogen salt generator and ozone generator in order to build up levels of ozone and the released halogen in the reservoir prior to providing the salt solution containing halogen and reaction products and the gaseous mixture containing air, ozone and the halogen to spray head 20. Advantages of the embodiments of FIGS. 2 and 3 are that many reactions occur that facilitate cleaning and sanitizing functions. Ozone, hydroxyl radicals, hydrogen peroxide, halogen sanitizers and hydroxides are provided to the spray or stream from opening 18 as it is emitted. By doing this, much more of the reactivity of the ozone, halogen and other chemicals is retained. In contrast, other systems that insert the ozone and other chemicals upstream from the sprayer head cause much of the reactivity of such chemicals to be lost because of rapid reaction times of these chemicals.

In another embodiment the water is heated to provide hot water, steam or hot vapor. An acid and redox controller can be added for electrolysis chamber 34 (FIG. 3) to control pH and ORP (oxidation reduction potential), with a controller cycling the chemical/ozone feed and supplying acid to electrolysis chamber 34. One or more metallic ionic additives, such as Silver, zinc, tin and copper, may be added to chamber 34 to provide a residual sanitizer to the spray.

Figure 4:
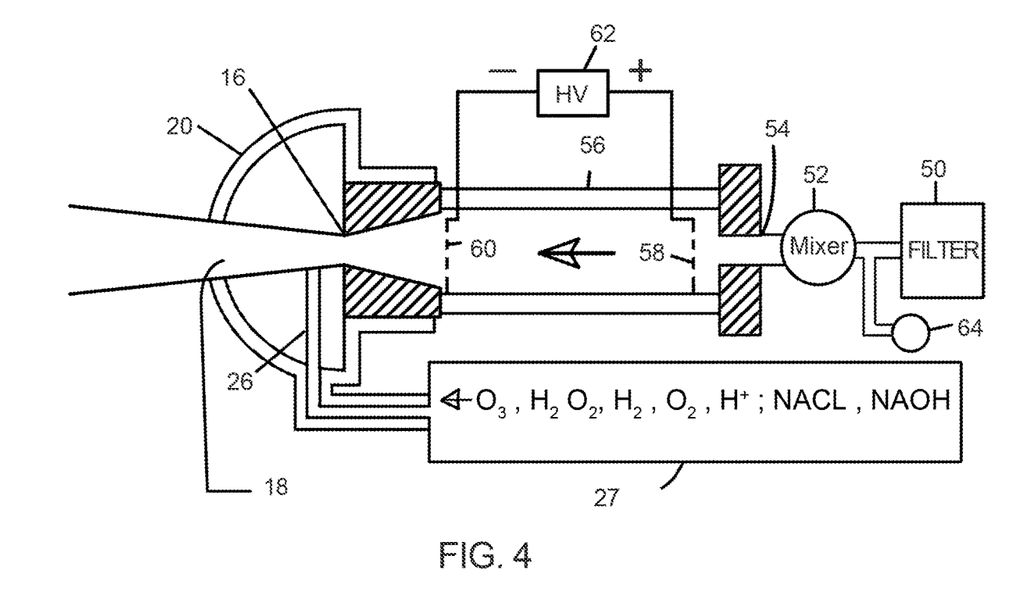
FIG. 4 is a block diagram of an electrostatic embodiment of the invention.

FIG. 4 illustrates an embodiment that uses electrostatic potentials to accelerate ionized components in a flow of water. Here, pressurized water is provided via a filter 50 to a mixer 52, and subsequently to an orifice 54. Orifice 54 is configured to provide a relatively fine spray of water to the interior of a chamber 56. A first screen, grid, mesh or the like 58 is provided within chamber 56 adjacent orifice 54, and a second screen, grid or the like 60 is provided as shown adjacent orifice 16. A high voltage source 62 provides a high voltage of 3000 volts or more and is connected as shown, with a positive potential applied to screen 58 and a negative potential applied to screen 60. A source of ionizible material, such as manganese, sodium, potassium or the like is applied to the flow of water from source 64 so that ions may be developed. In use, the electrostatic potential applied to screen 58 ionizes the ionizable material and creates ions in the spray of water from orifice 54. The ions are then accelerated by the potential on screen 60, pulling the spray out orifice 16 in a combination of a fine mist and vapor that is applied to surface to be sterilized, or to air in a room to be sterilized. As noted above, ozone and other substances are applied to the stream via tube 26. One possible advantage to this particular system is that the mist or vapor, being negatively charged, is attracted to and adheres to various surfaces. It is noted that the solids in the mist emitted at orifice 16 are in a very small quantity in order to not fog the air or create breathing problems, or create a dust on furniture.

Figure 5:
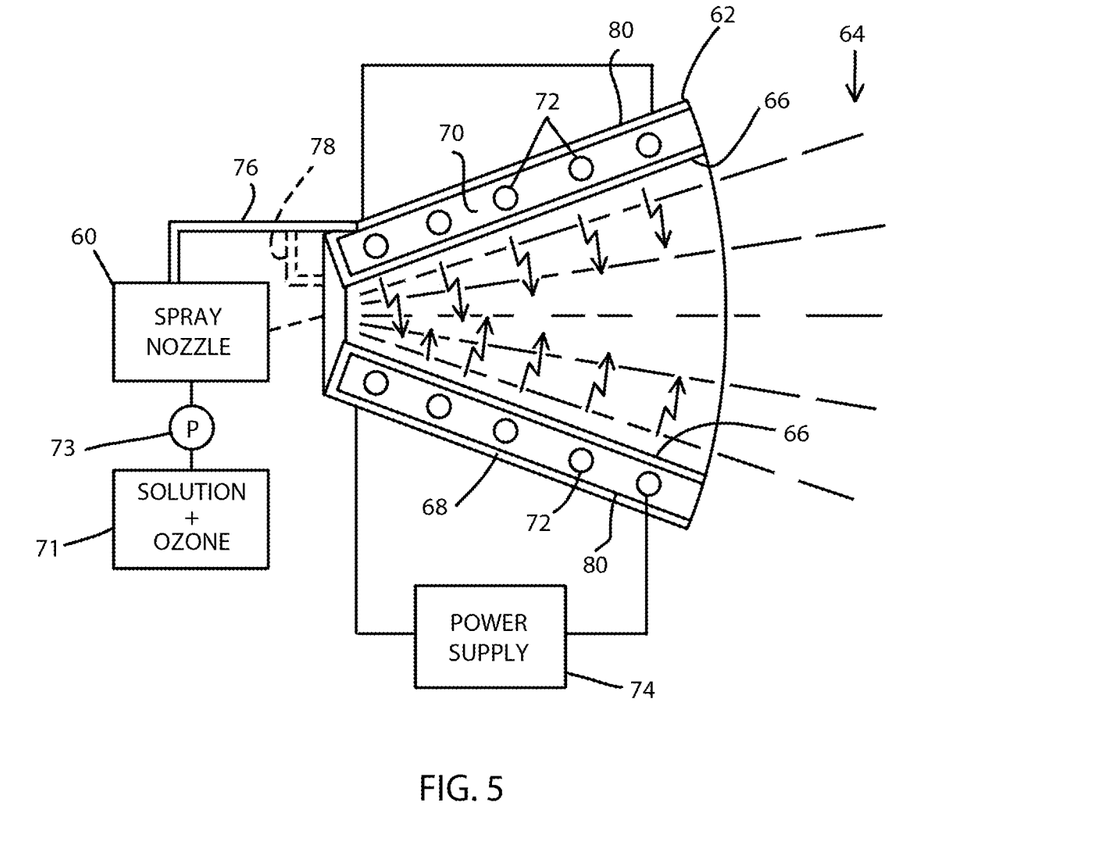
FIG. 5 is a cut-away, diagrammatic view showing an ultraviolet light dispensing hood or hood-like structure at the end of a spray or mist producing nozzle.

Referring to FIG. 5, another embodiment of a nozzle is shown. Here, any nozzle 60 configured for producing a controlled spray or mist of water or water based solution, such as a cleaning solution or solutions as described above, may be used. Likewise, a nozzle configured for controllably providing steam or steam with a hot spray or mist of water or water based cleaning solution may be used. The spray may be any spray, such as a trigger controlled spray from a pressure washer, or a less intense spray such as a spray used in a commercial dishwasher or carpet cleaner. A mist sprayer may also be used, such as a vegetable sprayer in a grocery store or the like. Other applications include icemakers where water is sprayed onto a chilled plate for freezing, thus sanitizing the water that is made into ice. In any case, a source of water, or a water-based solution 71 that may include ozone, is pumped by pump 73 or otherwise provided under pressure to nozzle 60. An enclosure, such as a hood or sheath 62, diagrammatically shown and cut away in FIG. 5, encloses or surrounds the spray or mist 64 as the spray or mist emerges from a nozzle 60. Hood 62 may be attached to nozzle 60 by any feasible means, such as bonding, threading the hood onto the nozzle by threads, attaching the hood to the nozzle with fasteners or constructing the hood integrally with the nozzle. In other embodiments, a space or plurality of spaces or openings may be provided between the hood and nozzle in order to draw air by Venturi action into the spray or mist from nozzle 60. In yet other embodiments, a hood 62 may be provided at outlet 24 of nozzle 10 as shown in FIG. 1. Hood 62 is configured as an ultraviolet radiator to irradiate spray or mist 64, particularly radiating ultraviolet radiation at the 254 nm wavelength band for breaking down most or all of the ozone and creating ozone reaction products in spray 64. In addition, the ultraviolet radiation is germicidal, and sterilizes the spray or mist. Accordingly, interior surface 66 of hood 62 are partially constructed having windows or regions through which ultraviolet light is passed, or interior surface 66 may be fully be constructed of an ultraviolet transparent material transparent to ultraviolet light, particularly around the 254 wavelength, and which may be of quartz, plastics, such as cyclic olefin copolymers, methyl-siloxane materials, some fluorocarbons such as fluorinatedethylenepropylene (FEP) and any other durable, waterproof material suitable for use with the fluid being sprayed. In other embodiments, both the 185 nm band and 254 nm band wavelengths from a mercury plasma lamp may be passed to the spray.

An exterior 68 of hood 62 is typically a material that blocks at least ultraviolet light from being transmitted for safety reasons, but may contain fluorescent compounds that glow in the presence of ultraviolet light. For aesthetic, artistic or other reasons, the solution sprayed or misted may be a phosphorescent material that glows for a period of time when excited by ultraviolet light, which would create a spray or mist of glowing droplets. For the same reasons, the solution may be a material that hardens by ultraviolet exposure during spraying or misting in order to create a solid or semi-solid mist or spray.

Figure 6:
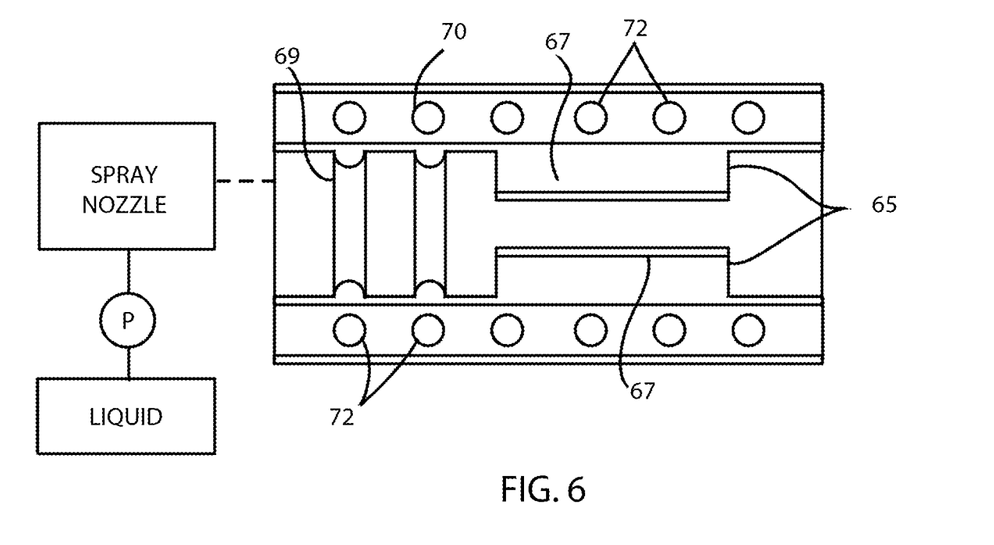
FIG. 6 is a cut away view of another embodiment of the invention.
Figure 7:
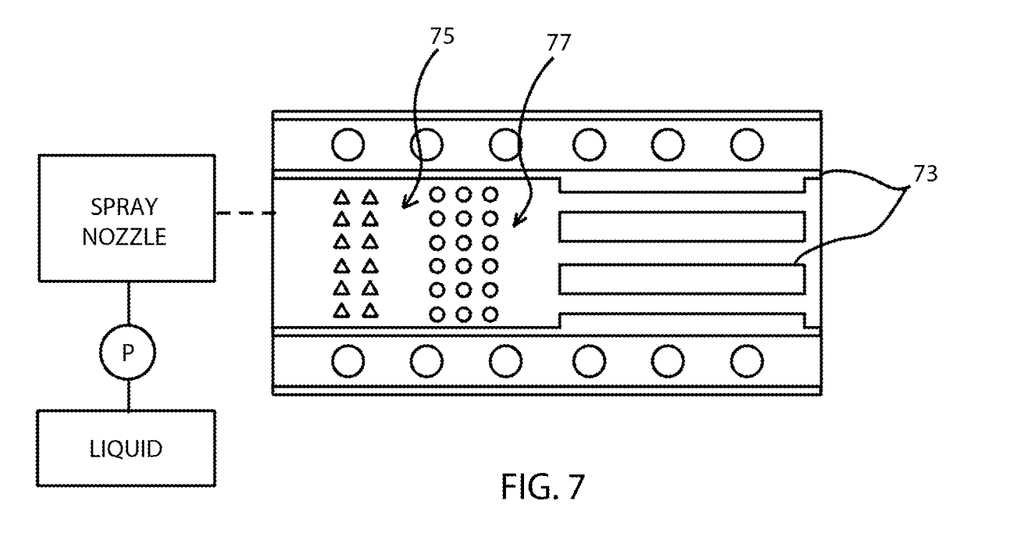
FIG. 7 is yet another embodiment of the invention.

An interior 70 of hood 62 may be generally hollow, and sealed at least along its interior from the spray or mist emitted by nozzle 60. Within interior 70 are ultraviolet emitter/emitters 72 that emit at least the aforementioned 254 nm band of ultraviolet light. Such emitters may be at least one mercury plasma lamp, such as a spiral mercury plasma lamp that spirals longitudinally around interior 70 of hood 62, or one or more mercury plasma lamps that are mounted lengthwise in interior 70. Such mercury plasma lamps emit ultraviolet radiation at both the 185 nm band and 254 nm band Other ultraviolet emitters may be ultraviolet LEDs, which may be configured to emit ultraviolet radiation only at the 255 wavelength, such as are available from ROITHNER LASER TECHNEK in Vienna, Austria, which commercially produces LEDs in the deep ultraviolet range down to 235 nm. Such LEDs would destroy ozone. Advances in LED technology should also see reasonably priced LEDs with wavelengths down to a 185 nm wavelength that produces ozone. Other techniques, such as frequency doubling or other optical techniques may be used to create wavelengths that create and destroy ozone. Fiber optic waveguides may be used where ultraviolet light is generated remotely from nozzle 60, the waveguides connected to transmit light into enclosure 62. In these instances, the LEDs or waveguides may be "potted" into or otherwise constructed integrally with hood 62 so that hood 62 is solid without being hollow, with interior wall 66, or one or more windows therein, passing the ultraviolet light. Where a mercury lamp is used, ultraviolet transparent inner surface 66 may be configured with a filter to filter out the 185 nm wavelength band and pass the 254 nm wavelength band in order to pass ultraviolet light that destroys ozone. In some embodiments, and as noted, both wavelengths may be passed by interior surface 66 in order to both create ozone and destroy the created ozone simultaneously in the spray or mist from nozzle 60. Such a spray or mist should be particularly effective for sanitization using ozone reaction products where outgassing or damage to a surface by ozone is not an issue. In other embodiments, ultraviolet transparent light guides that may have transparent optically modifying surfaces thereon may extend from the inner surface 66 or directly from ultraviolet emitters into or near mist or spray 64 in order to convey ultraviolet radiation into the spray or mist or closer to the spray or mist than inner surface 66. FIG. 6 shows blade-like light guides 65 generally parallel to the spray or mist, and having triangular edges 67 to disperse ultraviolet light directly into a spray. Here, the ultraviolet radiation is carried into the spray by the light guides and radiated outward perpendicular to the triangular edges 67. Such optically modifying surfaces may also be convex or cylindrical lens shapes that focus ultraviolet radiation into the spray or mist, or concave shapes that disperse the ultraviolet radiation into the spray or mist. For example, where a spiral mercury plasma lamp encircles the spray or mist, or straight lamps are disposed along a length of hood 62, inner surface 66 of hood 62 may be configured with one or more cylindrical lens 69 encircling a diameter of interior surface 62, or several cylindrical lenses 73 extending lengthwise along interior surface 66. Such lens shapes constructed integrally with inner surface 66 would focus concentrated bands of ultraviolet light into the spray or mist. Other light guide shapes on or extending from inner surface 66 may be dispersive arrays of triangles 75 (FIG. 7), optical gratings, arrays of lenses 77 or the like. Where the emitters are electrically powered at the nozzle, a power supply 74 provides electrical power to the emitters within interior 70. As noted, there may be embodiments where electrical power is not supplied to hood 62, as where ultraviolet light is provided by fiber optic light guides.

Ozone to be put in water or a solution to be sprayed or misted by nozzle 60 may be created by a remote ozone generator, as shown in FIGS. 2-4 and described in the accompanying respective discussions above, or ozone may be created within a hollow interior 70 where ultraviolet light emitters emit at around the 185 nm wavelength band. A short tube may convey the ozone to the nozzle where it is mixed with the water or solution to be sprayed, or the ozone may be provided to the spray or mist as the spray of mist enters hood 62, as shown by dashed line conduit 78 leading from interior 70 to the interior of hood 62. Where ozone is created within interior 70, one or more openings 80 would be provided to allow circulation of air to be ozonated through interior 70. Such openings would be protected from the spray or mist from nozzle 60, as by filtering, shielding or tubing connected to the openings and having an inlet or inlets remotely located from spray 64. Where ozone is created remotely as described above, such ozone may be diffused in water prior to being sprayed or misted by nozzle 60, or in a solution prior to being sprayed or dispersed by nozzle 60. In other embodiments, ozone may be pumped by an air pump to nozzle 60, as by forcing air through an ozone generator, with a connecting tube from the ozone generator to either nozzle 60 or to a gap between nozzle 60 and the upstream end of enclosure 62, or where enclosure 62 is affixed to nozzle 60, to one or more openings between nozzle and the upstream end of enclosure 62.

It is noted that while the shape of hood 62 is shown to be a truncated cone, such a shape is by way of example only. Hood 62 may be cylindrical, rounded with a slit exit for the spray or mist as shown in FIG. 1, or determined by design considerations.

It should be apparent that the components of my invention may be combined or assembled in any useful way, and that any of the mentioned compounds may be used separately or together, in any combination deemed to be useful for cleaning and sterilizing purposes.

We claim:

1. A method for dispensing a sanitizing composition comprising a carrier fluid, said method comprising:
    passing the carrier fluid, under pressure, through a spray nozzle and into a chamber mounted to the nozzle, wherein said chamber is positioned to receive the carrier fluid through a first opening of the chamber from an outlet of the nozzle into an interior of the chamber and wherein the chamber comprises a second opening on an opposite side from the first opening;
    providing ozone to the interior of the chamber so as to cause mixing of the ozone and the carrier fluid in the chamber; and
    irradiating the carrier fluid and the ozone with ultraviolet radiation as the carrier fluid and the ozone pass through the interior of the chamber to form ozone reaction products before exiting through the second opening.

2. The method of claim 1, wherein the chamber comprises an inner wall and an outer wall and a source of the ultraviolet radiation is located between the outer wall of the chamber and the inner wall of the chamber.

3. A method for dispensing a sanitizing composition comprising a carrier fluid, said method comprising:
    passing the carrier fluid, under pressure, through a spray nozzle and into a chamber mounted to the nozzle, wherein said chamber is positioned to receive the carrier fluid through a first opening of the chamber from an outlet of the nozzle into an interior of the chamber and wherein the chamber comprises a second opening on an opposite side from the first opening;
    providing ozone to the interior of the chamber so as to cause mixing of the ozone and the carrier fluid in the chamber; and
    irradiating the carrier fluid and the ozone with ultraviolet radiation as the carrier fluid and the ozone pass through the interior of the chamber to form ozone reaction products before exiting through the second opening;
    wherein the chamber comprises an inner wall and an outer wall and a source of the ultraviolet radiation is located between the exterior wall of the chamber and the inner wall of the chamber; and
    wherein the inner wall of the chamber is configured to direct the ultraviolet radiation into the interior of the chamber.

4. The method of claim 3, wherein a portion of the inner wall of the chamber is selectively transparent to a wavelength of ultraviolet light that decomposes the ozone into ozone reaction products within the chamber.

5. The method of claim 3, wherein said providing ozone to an interior of the chamber comprises creating the ozone between the inner wall of the chamber and an outer wall of the chamber using an ultraviolet light emitter located between the inner wall of the chamber and the outer wall of the chamber.

6. The method of claim 5, and further comprising providing the ozone created between the inner wall of the chamber and the outer wall of the chamber to the nozzle, the nozzle providing the ozone to the chamber.

7. The method of claim 5, and further comprising providing the ozone created between the interior wall of the chamber and the outer wall of the chamber to the interior of the chamber.

8. The method of claim 1, wherein said carrier fluid comprises water.

9. The method of claim 8, wherein said carrier fluid further comprises a substance in the water that reacts with the ozone to form sterilizing compounds.

10. The method of claim 9, wherein the-substance is selected from the group consisting of hydrogen peroxide, hydrogen, oxygen, hydrogen ions, sodium chloride, sodium hydroxide, and any combination of these.

11. A method for dispensing a sanitizing composition comprising a carrier fluid, said method comprising:
    passing the carrier fluid, under pressure, through a spray nozzle and into a chamber mounted to the nozzle, wherein said chamber is positioned to receive the carrier fluid through a first opening of the chamber from an outlet of the nozzle into an interior of the chamber and wherein the chamber comprises a second opening on an opposite side from the first opening;

providing ozone to the interior of the chamber so as to cause mixing of the ozone and the carrier fluid in the chamber; and irradiating the carrier fluid and the ozone with ultraviolet radiation as the carrier fluid and the ozone pass through the interior of the chamber to form ozone reaction products before exiting through the second opening;

wherein the chamber comprises an inner wall and an outer wall and a source of the ultraviolet radiation is located between the exterior wall of the chamber and the inner wall of the chamber; and wherein said providing ozone to an interior of the chamber comprises providing the ozone via a passage communicating between the chamber and a space between the outer wall of the chamber and the inner wall of the chamber.

* * * * *